United States Patent
Stawitz et al.

(10) Patent No.: US 6,713,146 B2
(45) Date of Patent: Mar. 30, 2004

(54) OPTICAL DATA STORES CONTAINING A CO-PHTHALOCYANINE COMPLEX IN THE INFORMATION LAYER RECORDABLE USING LIGHT

(75) Inventors: Josef-Walter Stawitz, Odenthal (DE); Horst Berneth, Leverkusen (DE); Thomas Bieringer, Odenthal (DE); Friedrich-Karl Bruder, Krefeld (DE); Rainer Hagen, Leverkusen (DE); Karin Hassenrück, Dësseldorf (DE); Serguei Kostromine, Swisttal (DE); Rafael Oser, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/961,157

(22) Filed: Sep. 20, 2001

(65) Prior Publication Data

US 2002/0127366 A1 Sep. 12, 2002

(30) Foreign Application Priority Data

| Sep. 21, 2000 | (DE) | ................................... 100 46 771 |
| Mar. 28, 2001 | (DE) | ................................... 101 15 227 |
| May 21, 2001 | (DE) | ................................... 101 24 585 |

(51) Int. Cl.$^7$ ................................................ B32B 3/02
(52) U.S. Cl. ................ 428/64.1; 428/64.8; 430/270.19; 430/270.2
(58) Field of Search ................ 428/64.1, 64.4, 428/64.8, 913; 430/270.14, 270.19, 270.2, 495.1, 945

(56) References Cited

U.S. PATENT DOCUMENTS

| 2,756,119 A | 7/1956 | Baumann et al. ................ 8/34 |
| 3,636,040 A | 1/1972 | Vollmann et al. ........ 260/314.5 |
| 5,248,538 A | 9/1993 | Kovacs et al. ................ 428/64 |
| 5,820,962 A | 10/1998 | Kimura et al. ............. 428/64.1 |

FOREIGN PATENT DOCUMENTS

| WO | 00/09522 | 2/2000 |
| WO | 0075922 | 12/2000 |

OTHER PUBLICATIONS

Yahya H K et al: "Synthesis of Some Colbalt Phthalocyanine–3,3' , 3,3'–Tetrasulphonamide S and Spectroscopic Studies of Their Application To Cellulosic Fibres" Journal of The Society of Dyers and Colourists, Society of Dyers and Colourists. Bradford, GB, Bd. 104, XP000025874 USSB:0037–9859 *Section Experimental*.

Angewandte Chemie, (month unavailable) 1978, pp. 927–1018, Von Klaus Deuchert und Siegfried Hünig, Mehrstufige organische Redoxsystemecin allgemeines Strukturprinzip.

Topics in Current Chemistry, vol. 92, (month unavailable), 1980, pp. 1–44, Siegfried Hünig and Horst Berneth, Two Step Reversible Redox Systems of the Weitz Type.

*Primary Examiner*—Elizabeth Mulvaney
(74) *Attorney, Agent, or Firm*—Godfried R. Akorli; Diderico van Eyl

(57) ABSTRACT

The present invention relates to a singly recordable optical data medium using Co-phthalocyanine complexes of the formula (I)

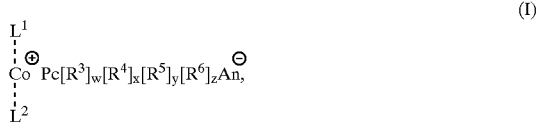

in which the groups are defined herein, as light-absorbing compounds in the information layer of optical data media, in which information layer is recordable using light, particularly for CD-R, and the application of the above-mentioned compounds to a polymer substrate, particularly polycarbonate, by spin coating.

10 Claims, No Drawings

OPTICAL DATA STORES CONTAINING A CO-PHTHALOCYANINE COMPLEX IN THE INFORMATION LAYER RECORDABLE USING LIGHT

BACKGROUND OF THE INVENTION

The present invention relates to the use of Co-phthalocyanine complexes and a light-absorbing compound in the information layer of recordable optical data media, which information layer is recordable using light, optical data media, and a process for their production.

The singly recordable compact disc (CD-R) has recently been experiencing an enormous growth in quantity. The light-absorbing compound of the information layer represents a substantial component of the optical data medium and has to meet correspondingly high and varied requirements. Not infrequently, the preparation of such compounds is correspondingly complicated (cf. WO-A 00/09522).

It is accordingly an object of the invention to provide a phthalocyanine dye that is simple to synthesize and meets the high requirements (such as light stability, advantageous signal/noise ratio, high recording sensitivity, damage-free application of the substrate material, and the like) for use as a light-absorbing compound in the information layer of a singly recordable optical data medium (chiefly CD-R).

It has surprisingly been found that Co-phthalocyanine complexes are suitable for this purpose.

SUMMARY OF THE INVENTION

The invention relates to an optical data medium containing a transparent substrate, on the surface of which are applied at least one recordable information layer that is recordable using light and optionally a reflection layer, optionally one or more intermediate layers, and/or optionally a protective layer, wherein the information layer contains, as a light-absorbing compound, at least one Co-phthalocyanine complex of the formula (I)

$$\begin{array}{c} L^1 \\ | \\ \overset{\oplus}{Co} \ Pc[R^3]_w[R^4]_x[R^5]_y[R^6]_z An, \overset{\ominus}{\phantom{x}} \\ | \\ L^2 \end{array} \quad (I)$$

in which

CoPc represents cobalt(III) phthalocyanine, $L^1$ and $L^2$ are axial, coordinately bonded ligands of the cobalt central atom and represent an amine of the formula $NR^0R^1R^2$ or represent an isonitrile of the formula $$\overset{\ominus}{IC}\!\!\equiv\!\!\overset{\oplus}{N}\!\!-\!\!R,$$

in which $R^0$, $R^1$, and $R^2$ independently of one another, represent hydrogen, alkyl, cycloalkyl, alkenyl, aryl, or hetaryl or two of the radicals $R^0$ to $R^2$, together with the N atom to which they are bonded, form a hydrogenated, partly hydrogenated, quasiaromatic, or aromatic ring (preferably a 5- to 7-membered ring) that optionally contains further heteroatoms (particularly from the group consisting of N, O, and/or S), R represents alkyl, cycloalkyl, alkenyl, aryl, or hetaryl, and $R^3$, $R^4$, $R^5$, and $R^6$ are substituents of phthalocyanine and, independently of one another, represent halogen, cyano, alkyl, aryl, alkylamino, dialkylamino, alkoxy, alkylthio, aryloxy, arylthio, $SO_3H$, $SO_2NR^7R^8$, $CO_2R^{12}$, $CONR^7R^8$, $NH\text{—}COR^{12}$, or a radical $-(B)_m-D$ in which B denotes a bridge member from the group consisting of a direct bond, $CH_2$, CO, CH(alkyl), $C(alkyl)_2$, NH, S, O, or $-CH=CH-$, such that $(B)_m$ denotes a chemically expedient sequence of bridge members B where m is 1 to 10 (preferably 1, 2, 3, or 4), D represents the monovalent radical of a redox system of the formula

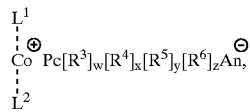

(Red)

or

(Ox)

or represents a metallocenyl radical or metallocenyl-carbonyl radical in which titanium, manganese, iron, ruthenium, or osmium is suitable as a metal center, in which $X^1$ and $X^2$, independently of one another, represent NR'R'', OR'', or SR'', $Y^1$ represents NR', O, or S, $Y^2$ represents NR', n represents 1 to 10, and R' and R'', independently of one another, represent hydrogen, alkyl, cycloalkyl, aryl, or hetaryl, or form a direct bond or a bridge to one of the C atoms of the $$-(CH=CH)_{\overline{n}}- \quad \text{or}$$

$$=\!(CH-CH)_{\overline{n}}\!=$$

chain, w, x, y, and z, independently of one another, represent 0 to 12 and w+x+y+z are 12, $R^7$ and $R^8$, independently of one another, represent alkylamino, hydroxy alkylamino, dialkylamino, bishydroxyalkylamino, or arylamino, or $R^7$ and $R^8$, together with the N atom to which they are bonded, form a heterocyclic 5-, 6-, or 7-membered ring, optionally with participation of further heteroatoms (particularly from the group consisting of O, N, and S, such that $NR^7R^8$ represents in particular pyrrolidino, piperidino, or morpholino), $R^{12}$ represents alkyl, aryl, hetaryl, or hydrogen, and $An^-$ represents an anion, particularly halide, $C_1$- to $C_{20}$-alkylCOO$^-$, formate, oxalate, lactate, glycolate, citrate, $CH_3OSO_3^-$, $NH_2SO_3^-$, $CH_3SO_3^-$, ½ $SO_4^{2-}$, or ⅓ $PO_4^{3-}$.

DETAILED DESCRIPTION OF THE INVENTION

The Co-phthalocyanine complex of the formula (I) may also be present in the form of formula (Ia)

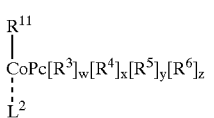

(Ia)

in which

CoPc, $L^2$, the radicals $R^3$–$R^6$, and the indices w, x, y, and z have the same meaning as in formula (I), and $R^{11}$ is a covalently bonded radical of the cobalt central atom and derived from the primary or secondary amine or from the isonitrile in the meaning of $L^1$ (i.e., —$NR^1R^2$, $R^1$ and $R^2$ having the above-mentioned meaning, or

For the sake of simplicity, however, the following statements all relate to the compounds of the formula (I) and, of course, also apply in the same manner to the formula (Ia).

Preferred heterocyclic amine ligands in the meaning of $L^1$ and $L^2$ are morpholine, piperidine, piperazine, pyridine, 2,2-bipyridine, 4,4-bipyridine, pyridazine, pyrimidine, pyrazine, imidazole, benzimidazole, isoxazole, benzisoxazole, oxazole, benzoxazole, thiazole, benzothiazole, quinoline, pyrrole, indole, and 3,3-dimethylindole, which are coordinated in each case at the nitrogen atom with the cobalt atom.

The alkyl, alkoxy, aryl, and heterocyclic radicals can optionally carry further radicals, such as alkyl, halogen, hydroxyl, hydroxyalkyl, amino, alkylamino, dialkylamino, nitro, cyano, CO—$NH_2$, alkoxy, alkoxycarbonyl, morpholino, piperidino, pyrrolidino, pyrrolidono, trialkylsilyl, trialkylsiloxy, or phenyl. The alkyl and alkoxy radicals may be saturated, unsaturated, straight-chain, or branched, the alkyl radicals may be partly halogenated or perhalogenated, and the alkyl and alkoxy radicals can be ethoxylated or propoxylated or silylated. Neighboring alkyl and/or alkoxy radicals on aryl or heterocyclic radicals can together form a three- or four-membered bridge.

Preferred compounds of the formula (I) are those in which the following are true for the radicals $R^0$ to $R^8$ and R, R', R", and $R^{12}$ and for the ligands $L^1$ and $L^2$:

substituents having the designation "alkyl" preferably denote $C_1$–$C_{16}$-alkyl (particularly $C_1$–$C_6$-alkyl), which are optionally substituted by halogen (such as chlorine, bromine, or fluorine), hydroxyl, cyano, and/or $C_1$–$C_6$-alkoxy;

substituents having the designation "alkoxy" preferably denote $C_1$–$C_{16}$-alkoxy (particularly $C_1$–$C_6$-alkoxy), which are optionally substituted by halogen (such as chlorine, bromine, or fluorine), hydroxyl, cyano, and/or $C_1$–$C_6$-alkyl;

substituents having the designation "cycloalkyl" preferably denote $C_4$–$C_8$-cycloalkyl (particularly $C_5$–$C_6$-cycloalkyl), which are optionally substituted by halogen (such as chlorine, bromine, or fluorine), hydroxyl, cyano, and/or $C_1$–$C_6$-alkyl;

substituents having the designation "alkenyl" preferably denote $C_6$–$C_8$-alkenyl, which are optionally substituted by halogen (such as chlorine, bromine, or fluorine), hydroxyl, cyano, and/or $C_1$–$C_6$-alkyl, particularly allyl;

substituents having the meaning "hetaryl" preferably represent heterocyclic radicals having 5- to 7-membered rings, which preferably contain heteroatoms selected from the group consisting of N, S, and/or O and are optionally fused to aromatic rings or optionally carry further substituents (for example halogen, hydroxyl, cyano, and/or alkyl), the following being particularly preferred: pyridyl, furyl, thienyl, oxazolyl, thiazolyl, imidazolyl, quinolyl, benzoxazolyl, benzothiazolyl, and benzimidazolyl, and the substituents having the designation "aryl" preferably denote $C_6$–$C_{10}$-aryl (particularly phenyl or naphthyl), which are optionally substituted by halogen (such as F or Cl), hydroxyl, $C_1$–$C_6$-alkyl, $C_1$–$C_6$-alkoxy, $NO_2$, and/or CN.

Preferred Co-phthalocyanine complexes of the formula (I) are those in which $L^1$ and $L^2$, independently of one another, represent ammonia, methyl-amine, ethylamine, ethanolamine, propylamine, isopropylamine, butylamine, isobutylamine, tert-butylamine, pentylamine tert-amylamine, benzylamine methylphenylhexylamine, aminopropylamine, aminoethylamine, 3-dimethylaminopropylamine, 3-diethylaminopropylamine, diethylaminoethylamine, dibutylaminopropylamine, morpholinopropylamine, piperidinopropylamine, pyrrolidinopropyl-amine, pyrrolidonopropylamine, 3-(methyl-hydroxyethylamino) pro-pylamine, methoxyethylamine, ethoxyethylamine, methoxypropyl-amine, ethoxypropylamine, methoxyethoxypropylamine, 3-(2-ethyl-hexyloxy) propylamine, isopropyloxyisopropylamine, dimethylamine, diethylamine, diethanolamine, dipropylamine, diisopropylamine, dibutylamine, diisobutylamine, di-tert-butylamine, dipentylamine, di-tert-amylamine, bis(2-ethylhexyl)amine, bis(aminoethyl)amine, bis(aminopropyl)amine, bis(dimethylaminopropyl)amine, bis(diethyl-aminopropyl)amine, bis(diethylaminoethyl)amine, bis(dibutylamino-propyl)amine, di(morpholinopropyl)amine, di(piperidinopropyl)-amine, di(pyrrolidinopropyl)amine, di(pyrrolidonopropyl)amine, bis(3-(methyl-hydroxyethylamino)propyl)amine, dimethoxyethyl-amine, diethoxyethylamine, dimethoxypropylamine, diethoxypropyl-amine, di(methoxyethoxyethyl)amine, di(methoxyethoxypropyl)-amine, bis(3-(2-ethylhexyloxy)propyl)amine, di(isopropoxyiso-propyl)amine, tripropylamine, tri(methoxyethoxyethyl)amine, tri(methoxyethoxypropyl)amine, diethylaminoethylpiperazine, dipropylaminoethylpiperazine, morpholine, piperidine, piperazine, pyridylamine, 2-thiazolylamine, 2-benzothiazolylamine, 2-benzox-azolylamine, 3-iminoisoindoleninylamine, pyridine, propylpyridine, butylpyridine, 2,2-bipyridine, 4,4-bipyridine, pyridazine, pyrimidine, pyrazine, imidazole, benzimidazole, isoxazole, benzisoxazole, oxazole, benzoxazole, thiazole, benzothiazole, quinoline, pyrrole, indole, 3,3-dimethylindole, aminopyridine, aniline, p-toluidine, p-tert-butylaniline, p-anisidine, isopropylaniline, butoxyaniline, or naphthyl-amine, or $L^1$ and $L^2$, independently of one another, represent methylisonitrile, ethyl-isonitrile, ethanolisonitrile, propylisonitrile, isopropylisonitrile, butyl-isonitrile, isobutylisonitrile, tert-butylisonitrile, pentylisonitrile, tert-amylisonitrile, benzylisonitrile, methylphenylhexylisonitrile, amino-propylisonitrile, aminoethylisonitrile, 3-dimethylaminopropylisonitrile, 3-diethylaminopropylisonitrile, diethylaminoethylisonitrile, dibutyl-aminopropylisonitrile, morpholinopropylisonitrile, piperidinopropyl-isonitrile, pyrrolidinopropylisonitrile, pyrrolidonopropylisonitrile, 3-(methyl-hydroxyethylamino)propylisonitrile, methoxyethylisonitrile, ethoxyethyl isonitrile, methoxypropylisonitrile, ethoxypropylisonitrile, methoxyethoxypropylisonitrile, 3-(2-ethylhexyloxy)propylisonitrile, isopropyloxyisopropylisonitrile, dimethylisonitrile, diethylisonitrile, diethanolisonitrile, dipropylisonitrile, diisopropylisonitrile, dibutyl-isonitrile, diisobutylisonitrile, di-tert-butylisonitrile, dipentylisonitrile, di-tert-amylisonitrile, bis(2-ethylhexyl)isonitrile, bis(aminoethyl)iso-nitrile, bis(aminopropyl)isonitrile, bis(dimethylaminopropyl)isonitrile, bis(diethylaminopropyl)isonitrile, bis(diethylaminoethyl)isonitrile, bis(dibutylaminopropyl)isonitrile, di(morpholinopropyl)isonitrile, di(piperidinopropyl)isonitrile, di(pyrrolidinopropyl)isonitrile, di(pyrrolidonopropyl)isonitrile, bis(3-(methyl-hydroxyethylamino)propyl)-isonitrile, dimethoxyethylisonitrile, diethoxyethylisonitrile, dimethoxy-propylisonitrile, diethoxypropylisonitrile, di(methoxyethoxyethyl)-isonitrile, di(methoxyethoxypropyl)isonitrile, bis(3-(2-ethylhexyloxy)-propyl)isonitrile, di(isopropyloxyisopropyl)isonitrile, tripropylisonitrile, tri(methoxyethoxyethyl)isonitrile, tri(methoxyethoxypropyl)isonitrile, pyridylisonitrile, 2-thiazolylisonitrile, 2-benzothiazolylisonitrile, 2-benzoxazolylisonitrile, 3-iminoisoindoleninylisonitrile, phenyliso-nitrile, p-tert-butylphenylisonitrile, p-methoxyphenylisonitrile, iso-propylphenylisonitrile, butoxyphenylisonitrile, or naphthylisonitrile, $R^3$, $R^4$, $R^5$, and $R^6$, independently of one another, represent chlorine, fluorine, bromine, iodine, cyano, methyl, ethyl, propyl, isopropyl, butyl, isobutyl, tert-butyl, pentyl, tert-amyl, hydroxyethyl, 3-dimethyl-aminopropyl, 3-diethylaminopropyl, phenyl, p-tert-butylphenyl, p-methoxyphenyl, isopropylphenyl, trifluoromethylphenyl, naphthyl, methylamino, ethylamino, propylamino, isopropylamine, butylamino, isobutylamino, tert-butylamino, pentylamino, tert-amylamino, benzylamino, methylphenylhexylamino, hydroxyethylamino, amino-propylamino, aminoethylamino, 3-dimethylaminopropylamino, 3-diethyla minopropylamino, diethylaminoethylamino, dibutylamino-propylamino, morpholinopropylamino, piperidinopropylamino, pyrrolidinopropylamino, pyrrolidonopropylamino, 3-(methyl-hydroxy-ethylamino)propylamino, methoxyethylamino, ethoxyethylamino, methoxypropylamino, ethoxypropylamino, methoxyethoxypropyl-amino, 3-(2-ethylhexyloxy)propylamino, isopropoxypropylamino, dimethylamino, diethylamino, diethanolamino, dipropylamino, diisopropylamino, dibutylamino, diisobutylamino, di-tert-butylamino, dipentylamino, di-tert-amylamino, bis(2-ethylhexyl)amino, bis-(aminopropyl)amino, bis(aminoethyl)amino, bis(3-dimethylamino-propyl)amino, bis(3-diethylaminopropyl)amino, bis(diethylamino-ethyl)amino, bis(dibutylaminopropyl)amino, di(morpholinopropyl)-amino, di(piperidinopropyl)amino, di(pyrrolidinopropyl)amino, di(pyrrolidonopropyl)amino, bis(3-(methyl-hydroxyethylamino)-propyl)amino, dimethoxyethylamino, diethoxyethylamino, dimethoxypropylamino, diethoxypropylamino, di(methoxyethoxy-ethyl)amino, di(methoxyethoxypropyl)amino, bis(3-(2-ethylhexyl-oxy)propyl)amino, di(isopropoxyisopropyl)amino, methoxy, ethoxy, propoxy, isopropoxy, butoxy, isobutoxy, tert-butoxy, pentyloxy, tert-amyloxy, methoxyethoxy, ethoxyethoxy, methoxypropoxy, ethoxy-propoxy, methoxyethoxypropoxy, 3-(2-ethylhexyloxy)propoxy, methylthio, ethylthio, propylthio, isopropylthio, butylthio, isobutylthio, tert-butylthio, pentylthio, tert-amylthio, phenyl, methoxyphenyl, trifluoromethylphenyl, naphthyl, $CO_2R^{12}$, $CONR^7R^8$, $NH-COR^{12}$, $SO_3H$, or $SO_2NR^7R^8$ or represent a radical of the formula

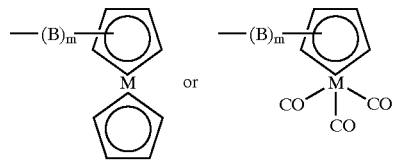

in which $(B)_m$ represents

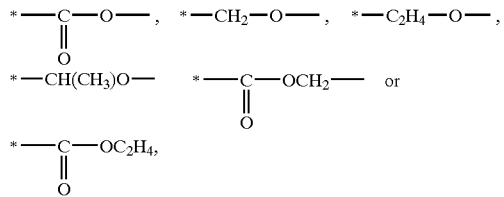

the asterisk (*) indicating the link to the 5-membered ring,

M represents an Mn or Fe cation, w, x, y, and z, independently of one another, represent 0 to 8 and w+x+y+z are 12, $An^-$ represents chloride, bromide, fluoride, $C_1$- to $C_{20}$-alkylCOO$^-$, formate, oxalate, lactate, glycolate, citrate, $CH_3OSO_3^-$, $NH_2SO_3^-$, $CH_3SO_3^-$, ½ $SO_4^{2-}$, or ⅓ $PO_4^{3-}$, $NR^7R^8$ represents amino, methylamino, ethylamino, propylamino, iso-propylamino, butylamino, isobutylamino, tert-butylamino, pentyl-amino, tert-amylamino, benzylamino, methylphenylhexylamino, 2-ethyl-1-hexylamino, hydroxyethylamino, aminopropylamino, amino-ethylamino, 3-dimethylaminopropylamino, 3-diethylaminopropyl-amino, morpholinopropylamino, piperidinopropylamino, pyrrolidinopropylamino, pyrrolidonopropylamino, 3-(methyl-hydroxyethyl-amino)propylamino, methoxyethylamino, ethoxyethylamino, methoxypropylamino, ethoxypropylamino, methoxyethoxypropyl-amino, 3-(2-ethylhexyloxy)propylamino, isopropyloxyisopropyl-amino, dimethylamino, diethylamino, dipropylamino, diisopropyl-amino, dibutylamino, diisobutylamino, di-tert-butylamino, dipentyl-amino, di-tert-amylamino, bis(2-ethylhexyl)amino, dihydroxyethyl-amino, bis(aminopropyl)amino, bis(aminoethyl)amino, bis(3-di-methylaminopropyl)amino, bis(3-diethylaminopropyl)amino, di(morpholinopropyl)amino, di(piperidinopropyl)amino, di(pyrrolidinopropyl)amino, di(pyrrolidonopropyl)amino, bis(3-(methyl-hydroxyethylamino)propyl)amino, dimethoxyethylamino, diethoxyethyl-amino, dimethoxypropylamino, diethoxypropylamino, di(methoxy-ethoxypropyl)amino, bis(3-(2-ethylhexyloxy)propyl)amino, di(iso-propyloxyisopropyl)amino, anilino, p-toluidino, p-tert-butylanilino, p-anisidino, isopropylanilino, or naphtylamino or $NR^7R^8$ represents pyrrolidino, piperidino, piperazino, or morpholino, $R^{12}$ represents hydrogen, methyl, ethyl, propyl, isopropyl, butyl, isobutyl tert-butyl, pentyl, tert-amyl, phenyl, p-tert-butylphenyl, p-methoxy-phenyl, isopropylphenyl, p-trifluoromethylphenyl, cyanophenyl, naphthyl, 4-pyridyl, 2-pyridyl, 2-quinolinyl, 2-pyrrolyi, or 2-indolyl, it being possible for the alkyl, alkoxy, aryl, and heterocyclic radicals optionally to carry further radicals, such as alkyl, halogen, hydroxyl, hydroxyalkyl, amino, alkylamino, dialkylamino, nitro, cyano, $CO-NH_2$, alkoxy, alkoxycarbonyl, morpholino, piperidino, pyrrolidino, pyrrolidono, trialkylsilyl, trialkylsiloxy, or phenyl, for the alkyl and/or alkoxy radicals to be saturated, unsaturated, straight-chain, or branched, for the alkyl radicals to be partially halogenated or perhalogenated, for the alkyl and/or alkoxy radicals to be ethoxylated or propoxylated or silylated, and for neighboring alkyl and/or alkoxy radicals on aryl or heterocyclic radicals together to form a three- or four-membered bridge.

In the context of this invention, redox systems are understood as meaning in particular the redox systems described in Angew. Chem. 1978, page 927, and in Topics of Current Chemistry, Vol. 92, page 1 (1980).

p-Phenylenediamines, phenothiazines, dihydrophenazines, bipyridinium salts (viologens), and quinodimethanes are preferred.

Particularly preferred Co complexes of the formula (I) are those that correspond to the formula (Ib)

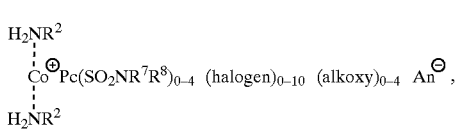

(Ib)

in which
halogen represents chlorine, bromine, or fluorine,
alkoxy represents $C_1-C_6$-alkoxy,
$R^7$ and $R^8$, independently of one another, have the above-mentioned meanings,
$An^\ominus$, CoPc, and $R^2$ likewise have the above-mentioned meanings.

The invention also relates to compounds of the formula (Ic)

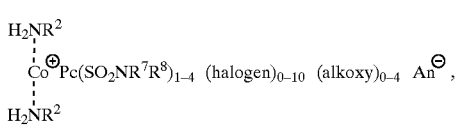

(Ic)

in which
halogen represents chlorine, bromine, or fluorine,
alkoxy represents $C_1-C_6$-alkoxy that is optionally substituted,
$R^7$ and $R^8$, independently of one another, have the above meanings, and
the other substituents have the above-mentioned meanings.

The invention also relates to a process for the preparation of compounds of the formula (Ic) by oxidizing a Co-phthalocyanine substituted by sulfonamido groups of the formula $SO_2NR^7R^8$, in which $R^7$ and $R^8$ have the above-mentioned meanings, and optionally by halogen and/or alkoxy, and then reacting the resultant oxidized intermediate with amines $L^1$ and $L^2$ (which are independently $NH_2R^2$).

The preparation is preferably carried out starting from a Co-phthalocyanine optionally substituted by halogen and/or alkoxy by sulfochlorination with chlorosulfonic acid and thionyl chloride at 50–130° C. and reaction of the resultant intermediate with the corresponding amine in water at pH 8–12 at from room temperature to 100° C. to give the amide. The subsequent introduction of the axial amine substituents is preferably effected in a known manner under oxidizing conditions, e.g., chlorine or air, preferably air, and, when using air, in the presence of excess amine (cf. Example 13). When using chlorine, the oxidation is carried out first and the amine is then added.

In addition to the compound of the formula (I), the information layer that is recordable using light particularly preferably additionally contains, as light-absorbing compounds, at least one other optionally substituted phthalocyanine with or without a central atom.

A suitable central atom is, for example, one from the group consisting of Si, Zn, Al, Cu, Pd, Pt, Au, and Ag, particularly Cu and Pd.

For example, the sulfonamido-substituted Cu-phthalocyanines disclosed in DE-A 19 925 712 are particularly preferred. Particularly preferred are those of the formula (II)

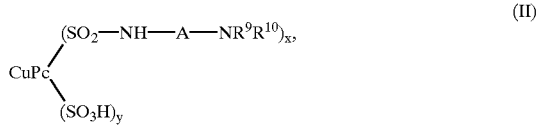

(II)

in which
CuPc represents a copper phthalocyanine radical,
A represents an optionally substituted straight-chain or branched $C_2-C_6$-alkylene, such as, for example, ethylene, propylene, butylene, pentylene, or hexylene,
$R^9$ and $R^{10}$, independently of one another, represent hydrogen or optionally substituted straight-chain or branched $C_1-C_6$-alkyl, such as, for example, methyl, ethyl, propyl, butyl, pentyl, hexyl, particularly substituted $C_1-C_6$-hydroxyalkyl and unsubstituted $C_1-C_6$-alkyl,
or $R^9$ and $R^{10}$, together with the N atom to which they are bonded, form a heterocyclic 5- or 6-membered ring that optionally contains a further heteroatom(e.g., S, N, or O),
x represents 2.0 to 4.0,
y represents 0 to 1.5, and
the sum of x and y is 2.0 to 4.0(preferably 2.5 to 4.0).

Particularly preferred components of the mixture are those of the formula (II) that correspond to the formula (IIa)

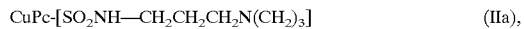

$CuPc-[SO_2NH-CH_2CH_2CH_2N(CH_2)_3]$ (IIa),

In which CuPc denotes copper phthalocyanine.

The sulfonamido- or amido-substituted phthalocyanines, as disclosed, for example, in EP-A 519,395, are suitable as further preferred additional light-absorbing compounds.

For mixtures of different light-absorbing compounds, the proportion of the compounds of the formula (I) is preferably 10 to 90% thereof. A mixture of the formulas (I) and (II) in a weight ratio of 10:90 to 90:10, preferably 20:80 to 80:20, particularly preferably of 40:60 to 60:40, is particularly preferred.

The information layer can also contain binders, wetting agents, stabilizers, diluents, and sensitizers and further components in addition to the light-absorbing compound.

The substrates can be produced from optically transparent plastics that, if necessary, have been provided with a surface treatment. Preferred plastics are polycarbonates and polyacrylates, as well as polycycloolefins or polyolefins.

The reflection layer can be produced from any metals or metal alloys that are usually used for recordable optical data media. Suitable metals or metal alloys can be applied by vapor deposition and sputtering and contain, for example, gold, silver, copper, aluminum, and alloys thereof with one another or with other metals.

The possible protective layer over the reflection layer may consist of UV-curable acrylates.

A possible intermediate layer that protects the reflection layer, for example, from oxidation, may likewise be present.

The invention furthermore relates to a process for the production of the optical data media according to the invention whereby the information layer that is recordable using light is applied to a transparent substrate by coating with at least one Co-phthalocyanine complex of the formula (I), optionally in combination with suitable binders, additives, and solvents, and is further optionally provided with a reflection layer, optionally further intermediate layers and optionally a protective layer.

The coating of the substrate with the light-absorbing compound of the formula (I) is optionally effected in combination with further dyes, binders, and/or solvents, preferably by spin coating.

For the coating, the light-absorbing compound of the formula (I) is preferably dissolved, with or without additives, in a suitable solvent or solvent mixture, so that the compound of the formula (I) accounts for 100% or less, for example, 10 to 20 parts by weight per 100 parts by weight of solvent. The recordable information layer is then metallized (i.e., to form a reflection layer), preferably under reduced pressure by sputtering or vapor deposition, and may then be provided with a protective coating (i.e., to form a protective layer) or with a further substrate or a covering layer. Multilayer arrangements having a semitransparent reflection layer are also possible.

Solvents or solvent mixtures for coating with the light-absorbing compounds of the formula (I) or their mixtures with additives and/or binders and other light-absorbing compounds are chosen on the one hand according to their solubility for the light-absorbing compound of the formula (I) and the other additives and on the other hand on the basis of a minimum effect on the substrate. Suitable solvents that have little effect on the substrate are, for example, alcohols, ethers, hydrocarbons, halogenated hydrocarbons, alkoxyalcohols, and ketones. Examples of such solvents are methanol, ethanol, propanol, 2,2,3,3-tetrafluoropropanol, butanol, diacetone alcohol, benzyl alcohol, tetrachloroethane, dichloro-methane, diethyl ether, dipropyl ether, dibutyl ether, methyl tert-butyl ether, methoxyethanol, ethoxyethanol, 1-methyl-2-propanol, methyl ethyl ketone, 4-hydroxy-4-methyl-2-pentanone, hexane, cyclohexane, ethylcyclohexane, octane, benzene, toluene, and xylene. Preferred solvents are hydro-carbons and alcohols since they have the slightest effect on the substrate.

Suitable additives for recordable information layer are stabilizers, wetting agents, binders, diluents, and sensitizers.

EXAMPLES

The following preparative examples illustrate the preparation of the dyes to be used according to the invention.

Example 1

115 g of Co-phthalocyanine were introduced into 1 liter of dry chlorobenzene at room temperature. 16 g of chlorine were passed in and stirring was effected for 30 min. After removal of the excess chlorine by blowing out with nitrogen, 90 g of 3-(methyl-hydroxyethyl)propylamine were added dropwise. Stirring was continued for 30 min at 90° C. and filtration with suction was effected after cooling to room temperature. Rinsing was effected with 1 liter of chlorobenzene and 1 liter of water, and the dye obtained was dried in vacuo. 156 g of dye of the formula

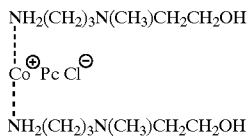

$\lambda_{max}$ 670 nm (NMP), were obtained.

The following compounds were prepared analogously by replacing the 3-(methyl-hydroxyethyl)propylamine by another amine or isonitrile in the same molar amount.

| Example | $L^1$ and $L^2$ | $R^3$–$R^6$ | $\lambda_{max}$ nm (NMP) |
|---|---|---|---|
| 2 | $H_2N$—$(CH_2)_{17}CH_3$ | H | 664 |
| 3 | $H_2N(CH_2)_3$—N⏜O | H | 669 |
| 4 | $H_2N(CH_2)_3N(CH_3)_2$ | H | 668 |
| 5 | $H_2N(CH_2)_3OCH_2CH_3$ | H | 665 |
| 6 | $H_2N$—CH(CH$_3$)—$CH_2$—$(OCH_2CH)_3$—NH, CH$_3$ | H | 666 |
| 7 | $H_2N$—CH(CH$_3$)—$CH_2$—O(CH(CH$_3$)—$CH_2$—O)$_{12}$ | H | 666 |
| 8 | $H_2N(CH_2)_3O$—$CH_2CH(CH_2CH_3)$—$(CH_2)_3CH_3$ | H | 667 |
| 9 | imidazole | H | 664 |
| 10 | C≡N—$C(CH_3)_3$ | H | 665 |

Example 11

80 g of nonabromo-chloro-Co-phthalocyanine were introduced into 1 liter of dry chlorobenzene at room temperature. 5 g of chlorine were passed in and stirring was effected for 30 min. After removal of the excess chlorine by blowing out with nitrogen, 28 g of 3-(methyl-hydroxyethyl)-propylamine were added dropwise. Stirring was continued for 30 min at 90° C. and filtration with suction was effected after cooling to room temperature. Rinsing was effected with 1 liter of the chlorobenzene and 1 liter of water, and the dye was dried in vacuo. 88 g of dye of the formula

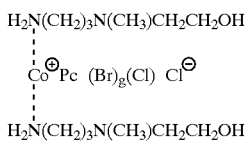

$\lambda_{max}$ 684 nm (NMP), were obtained.

The following compounds were prepared analogously by using the molar amount of another amine accordingly.

| Examples | L¹ and L² | R³ | R⁴ | R⁵—R⁸ | $\lambda_{max}$ nm (NMP) |
|---|---|---|---|---|---|
| 12 | Methoxy-ethoxy-propylamine | Br₉ | Cl | H | 685 |
| 13 | 3-Dimethyl-aminopropyl-amine | Br₉ | Cl | H | 684 |

Example 14

Sulfochlorination

| | | |
|---|---|---|
| 131 | g | of 98.8% cobalt phthalocyanine were introduced in the course of 30 min into |
| 394 | ml | of 98% chlorosulfonic acid. The batch was heated to 119° C. in the course of 25 min, stirred for 4 h at 119° C., and cooled to 85° C., and |
| 120 | ml | of thionyl chloride (at least 98%) were added dropwise at 85–88° C. in the course of 2 h; heating was then effected to 90–92° C. in the course of 20 min, stirring was effected for 4 h at 90–92° C., and stirring was then effected until RT was reached. |

Yield: 802 g of melt

Amide formation:

| | | |
|---|---|---|
| 381 | g | of melt were discharged onto |
| 1700 | g | of ice. Temperature –5° C. The precipitated sulfochloride was immediately filtered off with suction, washed neutral with |
| 1000 | ml | of ice water, and sucked thoroughly dry. The moist sulfochloride was immediately further processed. |
| 750 | g | of ice and |
| 750 | ml | of ice water were initially introduced. The sulfochloride was rapidly introduced into this mixture while stirring. |
| 39 | g | of 3-dimethylaminopropylamine were then added. The mixture was then heated to 80° C. in the course of 60 min. The pH was kept at pH 10.00 by means of 10% strength NaOH solution and the experiment was stirred for a further 45 minutes at 80° C. and pH 10.0. After cooling to room temperature, filtration with suction and washing with 1000 ml of water in portions were effected. The product was dried in a vacuum drying oven. |

Yield: 126.00 g

Introduction of the axial ligands 354 g of 3-dimethylaminopropylamine and 14 g of NH₄Cl were heated at 90° C. for 1 hour. After cooling to room temperature, 247 g of Co-phthalocyanine-tetrasulfo-3-dimethylaminopropylamide and 1 g of CoCl₂ were added. Air was then passed in for 10 hours. The mixture was added to 5 liter of water and filtered off. The dye was dried in vacuo. 275 g of dye of the formula

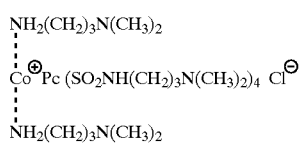

were obtained.

Example 15

Sulfochlorination:

| | | |
|---|---|---|
| 131 | g | of 98.8% cobalt phthalocyanine were introduced in the course of 30 min into |
| 394 | ml | of 98% chlorosulfonic acid. The batch was heated to 119° C. in the course of 25 min, stirred for 4 h at 119° C., and cooled to 85° C., and |
| 120 | ml | of thionyl chloride (at least 98%) were added dropwise at 85–88° C. in the course of 2 h; heating was then effected to 90–92° C. in the course of 20 min, stirring was effected for 4 h at 90–92° C., and stirring was then effected until RT is reached. |

Yield: 802 g of melt

Amide formation:

| | | |
|---|---|---|
| 381 | g | of melt were discharged onto |
| 1700 | g | of ice. Temperature –5° C. The precipitated sulfochloride was immediately filtered off with suction, washed neutral with |
| 1000 | ml | of ice water and sucked thoroughly dry. The moist sulfochloride was immediately further processed. |
| 750 | g | of ice and |
| 750 | ml | of ice water are initially introduced. The sulfochloride was rapidly introduced into this mixture while stirring. |
| 54 | g | of methoxyethoxypropylamine were then added. The mixture was then heated to 80° C. in the course of 60 min. The pH was kept at pH 10.00 by means of 10% strength NaOH solution and stirring was continued for 45 minutes at 80° C. and pH 10.0. After cooling to room temperature, filtration with suction and washing with 1000 ml of water in portions were effected. The product was dried in vacuo. |

Yield: 112 g

Introduction of axial ligands

| A mixture of |
|---|
| 199 g of Co-phthalocyanine-tetrasulfo-methoxyethoxypropylamide and |
| 280 g of imidazole was made up to about |
| 1000 ml with DMF and stirred for 24 h in an open beaker. |
| 1500 ml of water were added dropwise to this mixture. The product was filtered off and then washed with |
| 1000 ml of water. The dye was dried in vacuo. |
| 197 g of dye of the formula |

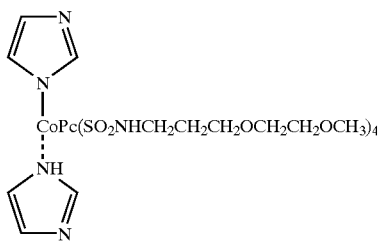

$\lambda_{max}$ 670 nm (NMP), were obtained.

20 g of diisobutylamine were then added. The mixture was then heated to 80° C. in the course of 60 min. The pH was kept at pH 10.00 by means of 10% strength NaOH solution and then stirring was effected for a further 45 minutes at 80° C. and pH 10.0.

After cooling to room temperature, filtration with suction and washing with 1000 ml of demineralized water in portions were effected.

The product was dried in vacuo.
Yield: 95 g

Introduction of Axial Ligands 354 g of 3-dimethylaminopropylamine and 14 g of NH$_4$Cl were heated at 90° C. for 1 hour. After cooling to room temperature, 219 g of Co-phthalocyanine-trisulfodiisobutylamide and 1 g of CoCl$_2$ were added. Air was then passed in for 10 hours. The mixture was added to 5 liter of water and filtered off. The dye was dried in vacuo. 240 g of dye of the formula

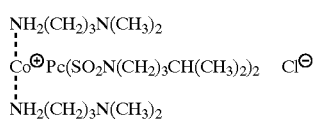

$\lambda_{max}$ 670 nm (NMP), were obtained.

The following compounds were prepared analogously by using the corresponding molar amount of another amine $L^1$ or $L^2$:

| Examples | $L^1$ and $L^2$ | $R^3$ | $R^4$ | $R^5$ | $R^6$ | $R^7$ | $R^8$ | $\lambda_{max}$ nm (NMP) |
|---|---|---|---|---|---|---|---|---|
| 17 | 3-Dimethyl-aminopropyl-amine | SO$_3$H | (SO$_2$NHR$^7$)$_3$ | H | H | 3-Dimethyl-aminopropyl | H | 671 |
| 18 | Methoxy-ethoxy-propylamine | Br$_2$ | Cl$_4$ | SO$_3$H | (SO$_2$NR$^8$R$^7$)$_3$ | Isobutyl | Isobutyl | 679 |
| 19 | 3-Dimethyl-aminopropyl-amine | (SO$_2$NHR$^7$)$_3$ | H | H | H | 3-Dimethyl-aminopropyl | H | 672 |

Example 16

Sulfochlorination

| |
|---|
| 131 g of 98.8% cobalt phthalocyanine were introduced into |
| 288 ml of 98% chlorosulfonic acid in the course of 30 min. The mixture was heated to 75° C. and stirred for 4 h at 75° C. After heating to 80° C., |
| 120 ml of thionyl chloride (at least 98%) were added dropwise in the course of 2 h. The mixture was stirred at 80° C. after 4 h and then stirred until RT was reached. |
| Yield: 712 g of melt |

Amide formation:

| |
|---|
| 402 g of melt were discharged onto |
| 1700 g of ice. The precipitated sulfochloride was immediately filtered off with suction, washed neutral with |
| 1000 ml of ice water, and sucked thoroughly dry. The moist sulfochloride was immediately further processed. |
| 750 g of ice and |
| 750 ml of ice water were initially introduced. The sulfochloride was rapidly introduced into this mixture while stirring. |

Example 20

32 g of 3-(methoxyethoxy)phthalonitrile and 385 ml of 1-butanol were heated to the boil, and 21 g of lithium were added. This mixture was heated for 1 h at 120° C. After cooling, 500 ml of water were added and filtration with suction was effected. Yield: 15 g of dye.

Introduction of the metal:

15 g of the green dye were added to 200 ml of DMF, and 2 g of CoCl$_2$ were added. The mixture was refluxed for 2 h. After cooling, 200 ml of water were added and filtration with suction was effected. Yield: 12 g of dye.

Introduction of Axial Ligands

A mixture of 12 g of dye and 24 g of imidazole was stirred with 200 ml of DMF in an open beaker for 24 h. 250 ml of water were added and filtration with suction was effected. The dye was dried in vacuo. 11 g of

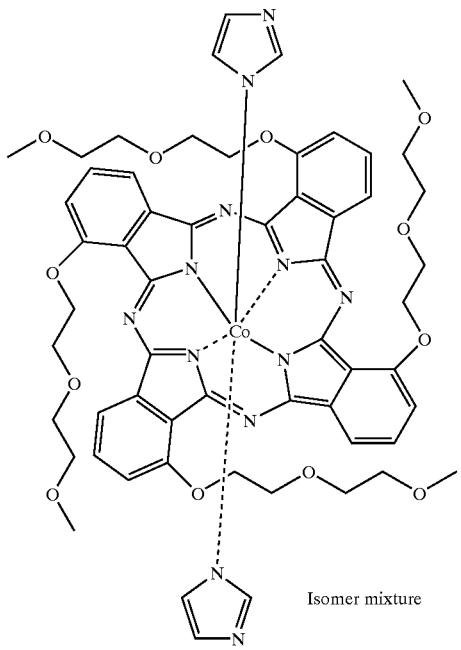

Isomer mixture dye of the formula $\lambda_{max}$ 715 nm (NMP), were obtained.

Example 21

The following compound was prepared analogously to the compound of Example 20:

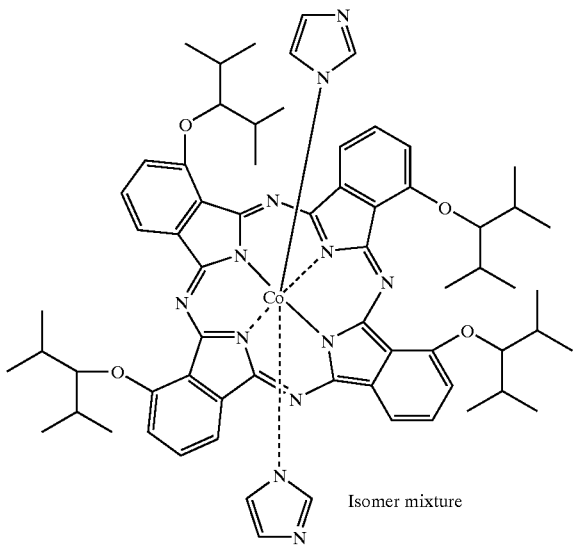

Isomer mixture $\lambda_{max}$ 718 nm (NMP).

Example 22

A 2% strength solution of a dye mixture of equal parts by weight of the CoPc complex from Example 5 and of the compound of the formula (IIa) in 2,2,3,3-tetrafluoropropanol was prepared at room temperature. This solution was applied to a pregrooved polycarbonate substrate by spin coating. The pregrooved polycarbonate was produced as a disc by injection molding. The dimensions of the disc and the groove structure corresponded to those which are usually used for CD-R. The disc having the dye layer as an information carrier was coated by vapor deposition with 100 nm of Ag. Thereafter, a UV-curable acrylate coating was applied by spin coating and cured by means of a UV lamp. A modulation height of 38% (30% to 70% is the CD-R specification) for the 3T signal and 62% (>60% is the CD-R specification) for the 11T signal was obtained, for example, at 12 mW recording power and single recording speed (1.4 m/s) during reading of the information using a commercial test recorder for CD-R (Pulstec® OMT 2000×4).

Example 23

A 2% solution of a dye mixture of equal parts by weight of the CoPc complex from Example 4 and of the compound of the formula (IIa) in 2,2,3,3-tetrafluoropropanol was prepared at room temperature. This solution was applied by means of spin coating. A modulation height of 32% (30% to 70% is the CD-R specification) for the 3T signal and 68% (>60% is the CD-R specification) for the 11T signal was obtained, for example, at 14 mW recording power and double recording speed (2.8 m/s) during reading of the information using a commercial test recorder for CD-R (Pulstec® OMT 2000×4).

Example 24

A 32% solution of a dye mixture of equal parts by weight of phthalogen blue of the Co-Pc complex from Example 4 and of the compound of the formula (IIa) in 10% strength acetic acid was prepared at room temperature. This stock solution was diluted to a dye content of 8% with diacetone alcohol. This solution was applied to the substrate by spin coating analogously to Example 22, and the substrate was provided with a reflection and protective layer analogously to Example 20. In a modification of Example 20, however, only 50 nm of Ag were applied as a reflection layer. A modulation height of 32% (30% to 70% is the CD-R specification) for the 3T signal and 67% (>60% is the CD-R specification) for the 11T signal was obtained, for example, at 8 mW recording power and single recording speed (1.4 m/s) during reading of the information using a commercial test recorder for CD-R (Pulstec OMT 2000×4).

Example 25

A 2% solution of the Co-phthalocyanine complex from Example 1 in 2,2,3,3-tetrafluoropropanol was prepared at room temperature. This solution was applied to the substrate by spin coating analogously to Example 22, and the substrate was provided with a reflection and protective layer analogously to Example 20. In a modification of Example 20, however, only 50 nm of Ag were applied as a reflection layer. A modulation height of 34% (30% to 70% is the CD-R specification) for the 3T signal and 62% (>60% is the CD-R specification) for the 11T signal were obtained, for example at 12 mW recording power and single recording speed (1.4 m/s) during reading of the information using a commercial test recorder for CD-R (Pulstec OMT 2000×4).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An optical data medium containing a transparent substrate, on the surface of which are applied at least one information layer that is recordable using light and optionally a reflection layer, optionally one or more intermediate layers, and/or optionally a protective layer wherein the information layer contains, as a light-absorbing compound, at least one Co-phthalocyanine dye of the formula (I)

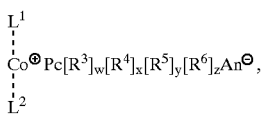
(I)

in which
CoPc represents cobalt(III) phthalocyanine,
$L^1$ and $L^2$ are axial, coordinately bonded ligands of the cobalt central atom and represent an amine of the formula $NR^0R^1R^2$ or represent an isonitrile of the formula

in which
$R^0$, $R^1$, and $R^2$ independently of one another, represent hydrogen, alkyl, cycloalkyl, alkenyl, aryl, or hetaryl or two of the radicals $R^0$ to $R^2$, together with the N atom to which they are bonded, form a hydrogenated, partly hydrogenated, quasiaromatic, or aromatic ring that optionally contains further heteroatoms,
R represents alkyl, cycloalkyl, alkenyl, aryl, or hetaryl, and
$R^3$, $R^4$, $R^5$, and $R^6$ are substituents of phthalocyanine and, independently of one another, represent halogen, cyano, alkyl, aryl, alkylamino, dialkylamino, alkoxy, aryloxy, arylthio, alkylthio, $SO_3H$, $SO_2NR^7R^8$, $CO_2R^{12}$, $CONR^7R^8$, $NH-COR^{12}$, or a radical $-(B)_m-D$ in which
B denotes a bridge member from the group consisting of a direct bond, $CH_2$, CO, CH(alkyl), C(alkyl)$_2$, NH, S, O, or $-CH=CH-$, such that $(B)_m$ denotes a chemically expedient combination of bridge members B where m is 1 to 10,
D represents the monovalent radical of a redox system of the formula

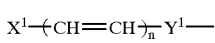 (Red)

or

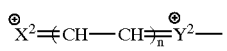 (Ox)

or represents a metallocenyl radical or metallocenylcarbonyl radical in which titanium, manganese, iron, ruthenium, or osmium is suitable as a metal center, in which
$X^1$ and $X^2$, independently of one another, represent NR'R", OR", or SR",
$Y^1$ represents NR', O, or S,
$Y^2$ represents NR',
n represents 1 to 10, and R' and R", independently of one another, represent hydrogen, alkyl, cycloalkyl, aryl, or hetaryl, or form a direct bond or a bridge to one of the C atoms of the

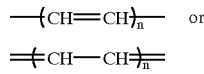

chain,
w, x, y, and z, independently of one another, represent 0 to 12 and w+x+y+z are 12,
$R^7$ and $R^8$, independently of one another, represent alkylamino, hydroxyalkylamino, dialkylamino, bishydroxyalkylamino, or arylamino, or $R^7$ and $R^8$, together with the N atom to which they are bonded, form a heterocyclic 5-, 6-, or 7-membered ring, optionally with participation of further heteroatoms,
$R^{12}$ represents alkyl, aryl, hetaryl, or hydrogen, and
$An^-$ represents an anion.

2. An optical data medium according to claim 1 wherein the information layer that is recordable using light contains at least one Co-phthalocyanine complex of the formula (I), in which the following are true for the radicals $R^0$ to $R^8$, R, R', R", $R^{12}$ and for the ligands $L^1$ and $L^2$:
substituents having the designation "alkyl" denote $C_1-C_{16}$-alkyl, which are optionally substituted by halogen, hydroxyl, cyano, and/or $C_1-C_6$-alkoxy,
substituents having the designation "alkoxy" denote $C_1-C_{16}$-alkoxy, which are optionally substituted by halogen, hydroxyl, cyano, and/or $C_1-C_6$-alkyl,
substituents having the designation "cycloalkyl" denote $C_4-C_8$-cycloalkyl, which are optionally substituted by halogen, hydroxyl, cyano, and/or $C_1-C_6$-alkyl,
substituents having the designation "alkenyl" denote $C_6-C_8$-alkenyl, which are optionally substituted by halogen, hydroxyl, cyano, and/or $C_1-C_6$-alkyl,
substituents having the designation "hetaryl" represent heterocyclic radicals having 5- to 7-membered rings, which are optionally fused to aromatic rings or optionally carry further substituents, and
the substituents having the designation "aryl" denote $C_6-C_{10}$-aryl, which are optionally substituted by halogen, hydroxyl, $C_1-C_6$-alkyl, $C_1-C_6$-alkoxy, $NO_2$, and/or CN.

3. An optical data medium according to claim 1 wherein the CoPc complex of the formula (I) corresponds to the formula (Ib)

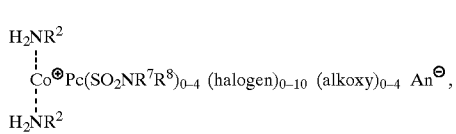 (Ib)

in which
CoPc represents cobalt(III) phthalocyanine,
halogen represents chlorine, bromine, or fluorine,
alkoxy represents $C_1-C_6$-alkoxy,
$R^2$ represents hydrogen, alkyl, cycloalkyl, alkenyl, aryl, or hetaryl,
$R^7$ and $R^8$, independently of one another, represent alkylamino, hydroxyalkylamino, dialkylamino, bishydroxyalkylamino, or arylamino, or $R^7$ and $R^8$, together with the N atom to which they are bonded, form a heterocyclic 5-, 6-, or 7-membered ring, optionally with participation of further heteroatoms, and
$An^-$ represents an anion.

4. An optical data medium according to claim 1 wherein the information layer that is recordable using light contains at least one Co-phthalocyanine complex of the formula (I), in which $L^1$ and $L^2$, independently of one another, represent ammonia, methyl-amine, ethylamine, ethanolamine, propylamine, isopropylamine, butylamine, isobutylamine, tert-butylamine, pentylamine tert-amylamine, benzylamine methylphenylhexylamine, aminopropylamine, aminoethylamine, 3-dimethylaminopropylamine, 3-diethylaminopropylamine, diethylaminoethylamine, dibutylaminopropylamine, morpholinopropylamine, piperidinopropylamine, pyrrolidinopropyl-amine, pyrrolidonopropylamine, 3-(methyl-hydroxyethylamino) pro-pylamine, methoxyethylamine, ethoxyethylamine, methoxypropyl-amine, ethoxypropylamine, methoxyethoxypropylamine, 3-(2-ethyl-hexyloxy) propylamine, isopropyloxyisopropylamine, dimethylamine, diethylamine, dipropylamine, diisopropylamine, diisobutylamine, di-tert-butylamine, dipentylamine, di-tert-amylamine, bis(2-ethylhexyl)-amine, bis(aminopropyl)amine, bis(aminoethyl)amine, bis(3-di-methylaminopropyl)amine, bis(3-diethylaminopropyl)amine, bis-(diethylaminoethyl) amine, bis(dibutylaminopropyl)amine, di(morpholinopropyl)amine, di(piperidinopropyl)amine, di(pyrrolidinopropyl)-amine, di(pyrrolidonopropyl) amine, bis(3-(methyl-hydroxyethyl-amino)propyl)amine, dimethoxyethylamine, diethoxyethylamine, dimethoxypropylamine, diethoxypropylamine, di(methoxyethoxy-ethyl)amine, di(methoxyethoxypropyl)amine, bis(3-(2-ethylhexyl-oxy)propyl)amine, di(isopropoxyisopropyl)amine, tripropylamine, tri(methoxyethoxyethyl)amine, tri(methoxyethoxypropyl)amine, diethylaminoethyl-piperazine, dipropylaminoethylpiperazine, morpholine, piperidine, piperazine, pyridylamine, 2-thiazolylamine, 2-benzothiazolylamine, 2-benzoxazolylamine, 3-iminoisoindoleninyl-amine, pyridine, propylpyridine, butylpyridine, 2,2-bipyridine, 4,4-bipyridine, pyridazine, pyrimidine, pyrazine, imidazole, benz-imidazole, isoxazole, benzisoxazole, oxazole, benzoxazole, thiazole, benzothiazole, quinoline, pyrrole, indole, 3,3-dimethyl-indole, aminopyridino, anilino, p-toluidine, p-tert-butylanilino, p-anisidine, isopropylanilino, butoxyanilino, or naphthylamino, or $L^1$ and $L^2$, independently of one another, represent methylisonitrile, ethyl-isonitrile, ethanolisonitrile, propylisonitrile, isopropylisonitrile, butyl-isonitrile, isobutylisonitrile, tert-butylisonitrile, pentylisonitrile, tert-amylisonitrite, benzylisonitrile, methylphenylhexylisonitrile, amino-propylisonitrile, aminoethylisonitrile, 3-dimethylaminopropylisonitrile, 3-diethylaminopropylisonitrile, diethylaminoethylisonitrile, dibutyl-aminopropylisonitrile, morpholinopropylisonitrile, piperidinopropyl-isonitrile, pyrrolidinopropylisonitrile, pyrrolidonopropylisonitrile, 3-(methyl-hydroxyethylamino)propylisonitrile, methoxyethylisonitrile, ethoxyethylisonitrile, methoxypropylisonitrile, ethoxypropylisonitrile, methoxyethoxypropylisonitrile, 3-(2-ethylhexyloxy)propylisonitrile, isopropyloxyisopropylisonitrile, dimethylisonitrile, diethylisonitrile, di-ethanolisonitrile, dipropylisonitrile, diisopropylisonitrile, dibutyliso-nitrile, diisobutylisonitrile, di-tert-butylisonitrile, dipentylisonitrile, di-tert-amylisonitrile, bis(2-ethylhexyl) isonitrile, bis(aminoethyl)iso-nitrile, bis(aminopropyl) isonitrile, bis(dimethylaminopropyl)isonitrile, bis (diethylaminopropyl)isonitrile, bis(diethylaminoethyl) isonitrile, bis(dibutylaminopropyl)isonitrile, di(morpholinopropyl)isonitrile, di(piperidinopropyl) isonitrile, di(pyrrolidinopropyl)isonitrile, di(pyrrolidonopropyl)isonitrile, bis(3-(methyl-hydroxyethylamino) propyl)iso-nitrile, dimethoxyethylisonitrile, diethoxyethylisonitrile, dimethoxy-propylisonitrile, diethoxypropylisonitrile, di(methoxyethoxyethyl)-isonitrile, di(methoxyethoxypropyl)isonitrile, bis(3-(2-ethylhexyloxy)-propyl)isonitrile, di(isopropyloxyisopropyl)isonitrile, tripropylisonitrile, tri(methoxyethoxyethyl)isonitrile, tri(methoxyethoxypropy)isonitrile, pyridylisonitrile, 2-thiazolylisonitrile, 2-benzothiazolylisonitrile, 2-benzoxazolylisonitrile, 3-iminoisoindoleninylisonitrile, phenyliso-nitrile, p-tert-butylphenylisonitrile, p-methoxyphenylisonitrile, iso-propylphenylisonitrile, butoxyphenylisonitrile, or naphthylisonitrile, $R^3$, $R^4$, $R^5$, and $R^6$, independently of one another, represent chlorine, fluorine, bromine, iodine, cyano, methyl, ethyl, propyl, isopropyl, butyl, isobutyl, tert-butyl, pentyl, tert-amyl, hydroxyethyl, 3-dimethyl-aminopropyl, 3-diethylaminopropyl, phenyl, p-tert-butylphenyl, p-methoxyphenyl, isopropylphenyl, trifluoromethylphenyl, naphthyl, methylamino, ethylamino, propylamino, isopropylamine, butylamino, isobutylamino, tert-butylamino, pentylamino, tert-amylamino, benzylamino, methylphenylhexylamino, hydroxyethylamino, aminopropylamino, aminoethylamino, 3-dimethylaminopropylamino, 3-diethyl-aminopropylamino, diethylaminoethyl-amino, dibutylamino-propylamino, morpholinopropylamino, piperidinopropylamino, pyrrolidinopropylamino, pyrrolidonopropylamino, 3-(methyl-hydroxy-ethylamino)propylamino, methoxyethylamino, ethoxyethylamino, methoxypropylamino, ethoxypropylamino, methoxyethoxypropyl-amino, 3-(2-ethylhexyloxy)propylamino, isopropoxypropylamino, dimethylamino, diethylamino, diethanolamino, dipropylamino, diisopropylamino, dibutylamino, diisobutylamino, di-tert-butylamino, dipentylamino, di-tert-amylamino, bis(2-ethylhexyl)amino, bis-(aminopropyl)amino, bis(aminoethyl)amino, bis(3-dimethylamino-propyl) amino, bis(3-diethylaminopropyl)amino, bis(diethylamino-ethyl) amino, bis(dibutylaminopropyl)amino, di(morpholinopropyl)-amino, di(piperidinopropyl)amino, di(pyrrolidinopropyl)amino, di(pyrrolidonopropyl) amino, bis(3-(methyl-hydroxyethylamino)-propyl)amino, dimethoxyethylamino, diethoxyethylamino, dimethoxypropylamino, diethoxypropylamino, di(methoxyethoxy-ethyl)amino, di(methoxyethoxypropyl)amino, bis(3-(2-ethylhexyl-oxy)propyl)amino, di(isopropoxyisopropyl)amino, methoxy, ethoxy, propoxy, isopropoxy, butoxy, isobutoxy, tert-butoxy, pentyloxy, tert-amyloxy, methoxyethoxy, ethoxyethoxy, methoxypropoxy, ethoxy-propoxy, methoxyethoxypropoxy, 3-(2-ethylhexyloxy)propoxy, phenyl, methylthio, ethylthio, propylthio, isopropylthio, butylthio, isobutylthio, tert-butylthio, pentylthio, tert-amylthio, methoxyphenyl, trifluoromethylphenyl, naphthyl, $CO_2R^{12}$, $CONR^7R^8$, $NH$—$COR^{12}$, $SO_3H$, or $SO_2NR^7R^8$ or represent a radical of the formula

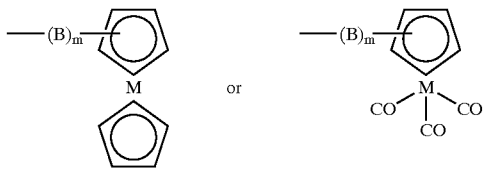

in which (B)$_m$ represents

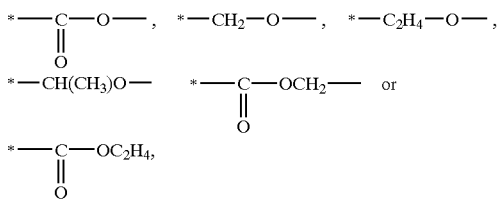

the asterisk (*) indicating the link to the 5-membered ring, w, x, y, and z, independently of one another, represent 0 to 8 and w+x+y+z are 12, An$^{31}$ represents chloride, bromide, fluoride, C$_1$- to C$_{20}$-alkylCOO$^-$, formate, oxalate, lactate, glycolate, citrate, CH$_3$OSO$_3^-$, NH$_2$SO$_3^-$, CH$_3$SO$_3^-$, ½ SO$_4^{2-}$, or ⅓ PO$_4^{3-}$, NR$^7$R$^8$ represents amino, methylamino, ethylamino, propylamino, iso-propylamino, butylamino, isobutylamino, tert-butylamino, pentyl-amino, tert-amylamino, benzylamino, methylphenylhexylamino, 2-ethyl-1-hexylamino, hydroxyethylamino, aminopropylamino, amino-ethylamino, 3-dimethylaminopropylamino, 3-diethylaminopropylamino, morpholinopropylamino, piperidinopropylamino, pyrrolidino-propylamino, pyrrolidonopropylamino, 3-(methyl-hydroxyethyl-amino)propylamino, methoxyethylamino, ethoxyethylamino, methoxypropylamino, ethoxypropylamino, methoxyethoxypropyl-amino, 3-(2-ethylhexyloxy)propylamino, isopropyloxyisopropyl-amino, dimethylamino, diethylamino, dipropylamino, diisopropyl-amino, dibutylamino, diisobutylamino, di-tert-butylamino, dipentyl-amino, di-tert-amylamino, bis(2-ethylhexyl)amino, dihydroxyethyl-amino, bis(aminopropyl)amino, bis(aminoethyl)amino, bis(3-dimethylaminopropyl)amino, bis(3-diethylaminopropyl)amino, di(morpholinopropyl)amino, di(piperidinopropyl)amino, di(pyrrolidinopropyl)amino, di(pyrrolidonopropyl)amino, bis(3-(methyl-hydroxyethylamino)propyl)amino, dimethoxyethylamino, diethoxyethylamino, dimethoxypropylamino, diethoxypropylamino, di(methoxyethoxypropyl)amino, bis(3-(2-ethylhexyloxy)propyl)amino, di(iso-propyloxyisopropyl)amino, anilino, p-toluidino, p-tert-butylanilino, p-anisidino, isopropylanilino, or naphthylamino or NR$^7$R$^8$ represents pyrrolidino, piperidino, piperazino, or morpholino, R$^{12}$ represents hydrogen, methyl, ethyl, propyl, isopropyl, butyl, isobutyl tert-butyl, pentyl, tert-amyl, phenyl, p-tert-butylphenyl, p-methoxy-phenyl, isopropylphenyl, p-trifluoromethylphenyl, cyanophenyl, naphthyl, 4-pyridyl, 2-pyridyl, 2-quinolinyl, 2-pyrrolyl, or 2-indolyl, wherein the alkyl, alkoxy, aryl, and heterocyclic radicals optionally carry further radicals, the alkyl and/or alkoxy radicals are optionally saturated, unsaturated, straight-chain, or branched, the alkyl radicals are optionally partially halogenated or perhalogenated, the alkyl and/or alkoxy radicals are optionally ethoxylated or propoxylated or silylated, and neighboring alkyl and/or alkoxy radicals on aryl or heterocyclic radicals together optionally form a three- or four-membered bridge.

5. An optical data medium according to claim 1 wherein the information layer that is recordable using light additionally contains a metal-containing or metal-free phthalocyanine differing from (I), wherein the central atom is selected from the group consisting of: Si, Zn, Al, Cu, Pd, Pt, Au, and Ag.

6. An optical data medium comprising a recordable information layer obtained by using light having a wavelength from 700 to 830 nm to record on an optical data medium according to claim 1.

7. A process for the production of the optical data medium according to claim 1 comprising applying the information layer that is recordable using light to a transparent substrate by coating the substrate with the Co-phthalocyanine complex of the formula (I), optionally in combination with suitable binders, additives, and suitable solvents, and optionally further providing the optical data medium with a reflection layer, further intermediate layers, and/or a protective layer.

8. An optical data store containing an information layer that is recordable using light, wherein the information layer comprises at least one light-absorbing Co-phthalocyanine complex of the formula (I)

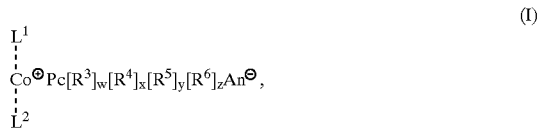

in which

CoPc represents cobalt(III) phthalocyanine,

L$^1$ and L$^2$ are axial, coordinately bonded ligands of the cobalt central atom and represent an amine of the formula NR$^0$R$^1$R$^2$ or represent an isonitrile of the formula

in which

R$^0$, R$^1$, and R$^2$ independently of one another, represent hydrogen, alkyl, cycloalkyl, alkenyl, aryl, or hetaryl or two of the radicals R$^0$ to R$^2$, together with the N atom to which they are bonded, form a hydrogenated, partly hydrogenated, quasiaromatic, or aromatic ring that optionally contains further heteroatoms, R represents alkyl, cycloalkyl, alkenyl, aryl, or hetaryl, and R$^3$, R$^4$, R$^5$, and R$^6$ are substituents of phthalocyanine and, independently of one another, represent halogen, cyano, alkyl, aryl, alkylamino, dialkylamino, alkoxy, aryloxy, arylthio, alkylthio, SO$_3$H, SO$_2$NR$^7$R$^8$, CO$_2$R$^{12}$, CONR$^7$R$^8$, NH—COR$^{12}$, or a radical —(B)$_m$—D in which B denotes a bridge member from the group consisting of a direct bond, CH$_2$, CO, CH(alkyl), C(alkyl)$_2$, NH, S, O, or —CH═CH—, such that (B)$_m$ denotes a chemically expedient combination of bridge members B where m is 1 to 10, D represents the monovalent radical of a redox system of the formula

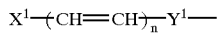 (Red)

or

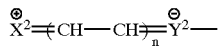 (Ox)

or represents a metallocenyl radical or metallocenyl-carbonyl radical in which titanium, manganese, iron, ruthenium, or osmium is suitable as a metal center, in which $X^1$ and $X^2$, independently of one another, represent NR'R", OR", or SR", $Y^1$ represents NR', O, or S, $Y^2$ represents NR', n represents 1 to 10, and R' and R", independently of one another, represent hydrogen, alkyl, cycloalkyl, aryl, or hetaryl, or form a direct bond or a bridge to one of the C atoms of the

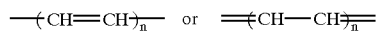

chain, w, x, y, and z, independently of one another, represent 0 to 12 and w+x+y+z are 12, $R^7$ and $R^8$, independently of one another, represent alkylamino, hydroxyalkylamino, dialkylamino, bishydroxyalkylamino, or arylamino, or $R^7$ and $R^8$, together with the N atom to which they are bonded, form a heterocyclic 5-, 6-, or 7-membered ring, optionally with participation of further heteroatoms, $R^{12}$ represents alkyl, aryl, hetaryl, or hydrogen, and An⁻ represents an anion.

9. A compound of the formula (Ic)

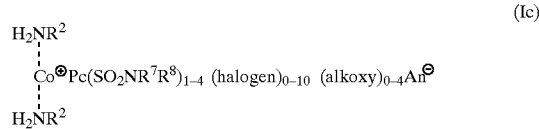 (Ic)

in which

CoPc represents cobalt(III) phthalocyanine, $R^7$ and $R^8$, independently of one another, represent alkylamino, hydroxyalkylamino, dialkylamino, bishydroxyalkylamino, or arylamino, or $R^7$ and $R^8$, together with the N atom to which they are bonded, form a heterocyclic 5-, 6-, or 7-membered ring, optionally with participation of further heteroatoms, halogen represents chlorine, bromine, or fluorine, alkoxy represents $C_1$–$C_6$-alkoxy that is optionally substituted, and An⁻ represents an anion.

10. A process for the preparation of the compound according to claim 9 comprising (1) oxidizing a Co-phthalocyanine substituted by sulfonamido groups of the formula $SO_2NR^7R^8$, in which $R^7$ and $R^8$ are defined as for formula (Ic), and optionally by halogen and/or alkoxy, and (2) reacting the oxidized Co-phthalocyanine with amines $L^1$ and $L^2$, wherein $L^1$ and $L^2$ independently represent an amine of the formula $NH_2R^2$ in which $R^2$ represents hydrogen, alkyl, cycloalkyl, alkenyl, aryl, or hetaryl.

* * * * *